(12) United States Patent
Hikita

(10) Patent No.: US 7,732,562 B2
(45) Date of Patent: Jun. 8, 2010

(54) TRISOXETANE COMPOUND, PRODUCTION PROCESS AND OPTICAL WAVEGUIDE THEREWITH

(75) Inventor: Takami Hikita, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 551 days.

(21) Appl. No.: 11/783,206

(22) Filed: Apr. 6, 2007

(65) Prior Publication Data

US 2007/0237963 A1 Oct. 11, 2007

(30) Foreign Application Priority Data

Apr. 6, 2006 (JP) ............... 2006-105203

(51) Int. Cl.
*C07D 305/00* (2006.01)
*C08G 65/40* (2006.01)
*G02B 6/10* (2006.01)

(52) U.S. Cl. ............... 528/405; 385/131; 549/510

(58) Field of Classification Search ............... None
See application file for complete search history.

(56) References Cited

U.S. PATENT DOCUMENTS 6,611,651 B1 8/2003 Ogawa et al.

FOREIGN PATENT DOCUMENTS

| JP | 6-16804 A | 1/1994 |
| JP | 11-106380 A | 4/1999 |
| JP | 2000-356720 A | 12/2000 |
| JP | 2001-31665 A | 2/2001 |
| JP | 2002-322268 A * | 11/2002 |
| JP | 2003-147045 A | 5/2003 |
| JP | 2004-352622 A * | 12/2004 |
| JP | 2006-151859 A * | 6/2006 |
| JP | 2007-70320 A * | 3/2007 |
| JP | 2007-70322 A * | 3/2007 |

OTHER PUBLICATIONS

XP-002437803—Abstract "Novel synthesis of oxetane resins from multifunctional oxetane compunds and cyclic carboxylic anhydrides" (JP 2002 322268).

* cited by examiner

*Primary Examiner*—Robert Sellers
(74) *Attorney, Agent, or Firm*—Sughrue Mion, PLLC

(57) ABSTRACT

The present invention relates to a trisoxetane compound represented by the following formula (1):

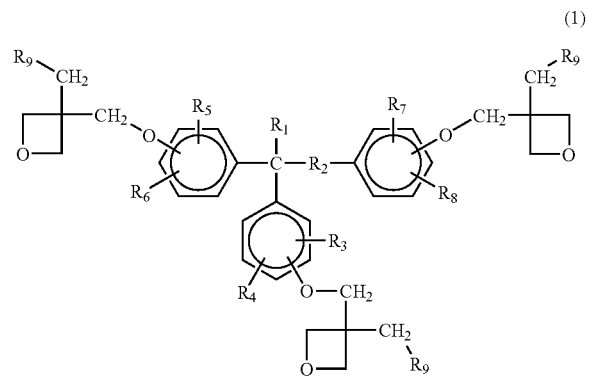

(1)

wherein $R_1$ and $R_3$ to $R_8$ are the same or different and each represents a hydrogen atom or an alkyl group having 1 to 6 carbon atom(s) with the proviso that at least one of $R_3$ to $R_8$ is an alkyl group having 1 to 6 carbon atom(s); $R_2$ represents a divalent aliphatic chained organic group having 0 to 16 carbon atom(s); and $R_9$'s each represents a hydrogen atom or an alkyl group having 1 to 6 carbon atom(s), a process for producing the same, and an optical waveguide including the same.

5 Claims, 2 Drawing Sheets

TRISOXETANE COMPOUND, PRODUCTION PROCESS AND OPTICAL WAVEGUIDE THEREWITH

FIELD OF THE INVENTION

The present invention relates to a trisoxetane compound having an oxetane ring which is capable of cationic polymerization, a process for producing the same, and an optical waveguide including the same. The photocurable resin composition and a heat curable resin composition containing the trisoxetane compound are excellent in heat resistance, mechanical property, reduced water absorbing property, coating flatness, and adhesion.

BACKGROUND OF THE INVENTION

An oxetane compound has recently attracted attention as a monomer capable of photo-initiated cationic polymerization or curing, and various oxetane compound synthesis methods have been proposed along with developments of many monofunctional and polyfunctional oxetane compounds.

As such oxetane compound, an oxetane compound represented by the following formula (4)

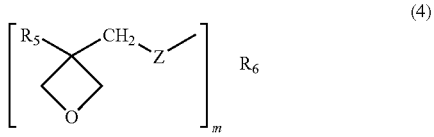

(4)

(wherein $R_5$ is a hydrogen atom, a fluorine atom, an alkyl group having 1 to 6 carbon atom(s), a fluoroalkyl group having 1 to 6 carbon atom(s), an allyl group, an aryl group, a furyl group, or a thienyl group; $R_6$ is a group selected from a chained or branched poly(alkyleneoxy) group, a xylylene group, a siloxane bond, and an ester bond; Z is an oxygen atom or a sulfur atom; and m is an integer of 2 to 4), is disclosed in a patent document (see Patent document 1).

Further, a biphenyl derivative having an oxetane ring represented by the following formula (5)

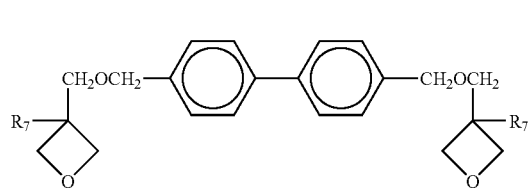

(5)

(wherein $R_7$ is a hydrogen atom or an alkyl group having 1 to 6 carbon atom(s)), and a biphenyl derivative having an oxetane ring represented by the following formula (6)

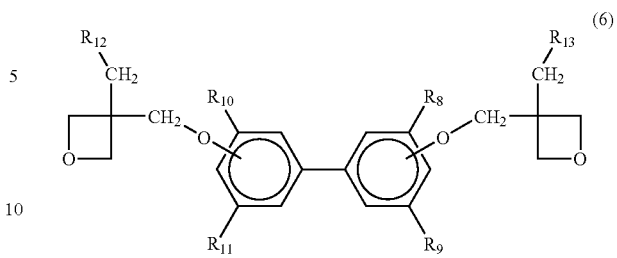

(6)

(wherein each of $R_8$ to $R_{11}$ represents a hydrogen atom or a methyl group; and each of $R_{12}$ and $R_{13}$ represents a hydrogen atom or an alkyl group having 1 to 6 carbon atom(s)) have been also proposed (see Patent Documents 2 and 3).

The above compounds are generally obtainable by using an alkali metal such as sodium hydroxide and potassium hydroxide as a base and synthesizing oxetane ester sulfonate and a divalent phenol compound corresponding to the oxetane ester sulfonate under the presence of the base. In addition, a phase transfer catalyst such as a quaternary ammonium salt is used according to the necessity in order to increase a yield of the compounds in the synthesis. Further, the oxetane compounds have heretofore been used as a material for coating compositions and adhesives for the purposes of increasing heat resistance, adhesion, and the like, and a use of the oxetane compound as a material for forming an optical waveguide has recently been proposed (see Patent Documents 4 and 5). The optical waveguide is incorporated into an optical waveguide device, an optical integrated circuit, and an optical wiring board and is used widely in the fields of optical communication, optical information processing, and like general optics.

Patent Document 1: JP-A-6-16804
Patent Document 2: JP-A-11-106380
Patent Document 3: JP-A-2001-31665
Patent Document 4: JP-A-2000-356720.
Patent Document 5: JP-A-2003-147045

SUMMARY OF THE INVENTION

However, among the oxetane compounds, biphenyl derivative is a compound having a low molecular weight and has a low viscosity that makes it difficult to form a thick film on a substrate, for example. Further, due to the bifunctionality, the biphenyl derivative undesirably requires a long time for curing. Furthermore, the oxetane compounds other than the biphenyl derivative have problems that it is difficult to form a desired thick film as well as to achieve a desired curability.

When such conventional oxetane compounds are used as the material for forming the optical waveguide, since it is difficult to stably cure optical waveguides having an identical shape, there are problems that waveguide characteristic is fluctuated and that it is difficult to form a thick film in a convenient manner.

Further, the conventional oxetane compound synthesis methods have a problem that introduction of an oxetanyl group does not proceed quantitatively to result in a low yield of a desired oxetane compound. In addition, since a compound having a non-reacted hydroxyl group is generated as a byproduct, complicated operation is often required for obtaining the desired oxetane compound.

The invention has been accomplished in view of the above-described circumstances, and an object thereof is to provide a novel trisoxetane compound which enables producing a polymer excellent in thick film formation property, curability, heat resistance, and the like, a process for producing the same, and an optical waveguide including the same.

DESCRIPTION OF REFERENCE NUMERALS AND SIGNS

Figure 1:
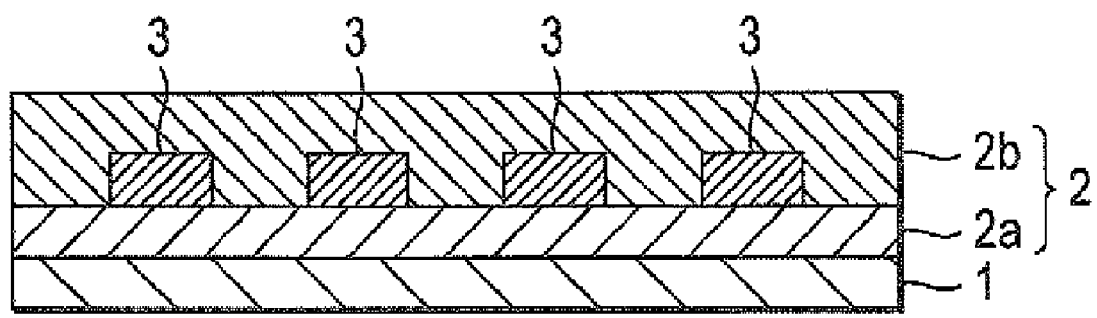
FIG. 1 is a horizontal sectional view showing one example of an optical waveguide of the invention.

1: substrate
2: cladding layer
3: core

DETAILED DESCRIPTION OF THE INVENTION

Namely, the present invention relates to the following (1) to (5).

(1) A trisoxetane compound represented by the following formula (1):

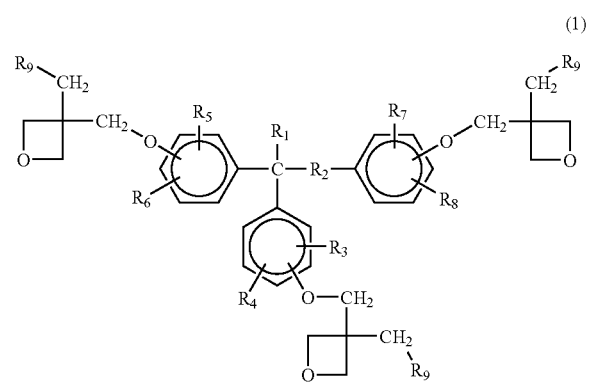

(1)

wherein $R_1$ and $R_3$ to $R_8$ are the same or different and each represents a hydrogen atom or an alkyl group having 1 to 6 carbon atom(s) with the proviso that at least one of $R_3$ to $R_8$ is an alkyl group having 1 to 6 carbon atom(s);
$R_2$ represents a divalent aliphatic chained organic group having 0 to 16 carbon atom(s); and
$R_9$'s each represents a hydrogen atom or an alkyl group having 1 to 6 carbon atom(s).

(2) A process for producing the trisoxetane compound according to (1), which comprises:
reacting a phenolic compound represented by the following formula (2):

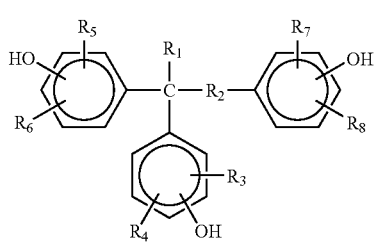

(2)

wherein $R_1$ and $R_3$ to $R_8$ are the same or different and each represents a hydrogen atom or an alkyl group having 1 to 6 carbon atom(s) with the proviso that at least one of $R_3$ to $R_8$ is an alkyl group having 1 to 6 carbon atom(s), and $R_2$ represents a divalent aliphatic chained organic group having 0 to 16 carbon atom(s), with a cesium salt to thereby obtain a cesium phenolate; and
reacting the cesium phenolate with an ester sulfonate of 3-alkyl-3-hydroxymethyloxetane represented by the following formula (3):

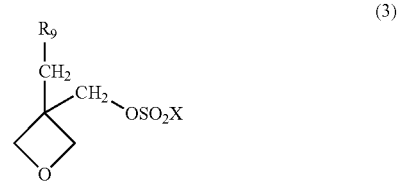

(3)

wherein $R_9$ represents a hydrogen atom or an alkyl group having 1 to 6 carbon atom(s), and X represents a methyl group, an ethyl group, a phenyl group, or a tolyl group.

(3) The process according to (2), wherein the cesium salt is cesium carbonate.

(4) An optical waveguide comprising:
a substrate;
a cladding layer disposed on the substrate; and
a core having a predetermined pattern and disposed on the cladding layer, which transmits an optical signal,
wherein at least one of the cladding layer and the core is constituted of a resin composition containing a trisoxetane compound represented by the following formula (1):

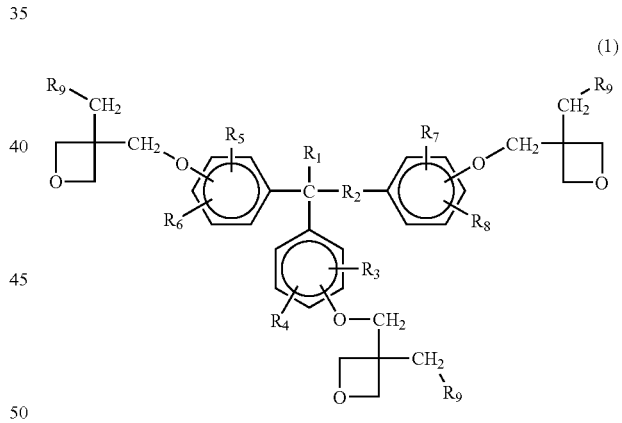

(1)

wherein $R_1$ and $R_3$ to $R_8$ are the same or different and each represents a hydrogen atom or an alkyl group having 1 to 6 carbon atom(s) with the proviso that at least one of $R_3$ to $R_8$ is an alkyl group having 1 to 6 carbon atom(s);
$R_2$ represents a divalent aliphatic chained organic group having 0 to 16 carbon atom(s); and
$R_9$'s each represents a hydrogen atom or an alkyl group having 1 to 6 carbon atom(s).

(5) The optical waveguide according to (4), wherein at least one of the cladding layer and the core is constituted of a resin composition containing the trisoxetane compound and a compound having an epoxy group or a vinylether group.

The inventors of the invention have sought an oxetane compound which enables producing a polymer that is excellent in heat resistance, mechanical property, and the like and effectively used as a material for coating compositions, coating materials, adhesives, lenses, optical waveguides, and the like and have conducted extensive researches. As a result of syntheses of various compounds each having a specific structure and many experiments, they have found that it is possible to attain the above-described object by using the novel trisoxetane compound represented by the above formula (1), thereby accomplishing the invention. More specifically, since the novel compound has three oxetane rings in one molecule, the novel compound has a rapid curing property, and since the cured products thereof forms a high density network structure, the cured products has excellent heat resistance and the like. Further, since the novel compound has a high molecular weight unlike the conventional compounds each having a low molecular weight, the novel compound has a high viscosity to be advantageous for forming a thick film, particularly when used as a material for forming an optical waveguide (cladding layer and core) since it is possible to cure optical waveguides having an identical shape in a stable manner, thereby achieving effects of maintaining identical waveguide characteristic and the like.

Meanwhile, the inventors have made intensive studies also on a synthesis method that enables the novel compound to be synthesized at high yield. As a result, they have found that it is possible to synthesize the novel compound at high yield by reacting the phenolic compound represented by the formula (2) with the ester sulfonate of 3-alkyl-3-hydroxymethyloxetane represented by the formula (3) under predetermined conditions, particularly with the use of the cesium salt as a base.

As described above, the invention relates to the novel trisoxetane compound represented by the formula (1). Since this compound has a high molecular weight unlike the conventional compounds having low molecular weights, this compound has such a high viscosity that makes it easy to form a thick film. In addition, since the compound has three oxetane rings in one molecule, the compound is able to be rapidly cured by light or heat. Therefore, a photocurable resin composition and a heat curable resin composition containing the trisoxetane compound of the invention are excellent in curability, heat resistance, toughness, and mechanical property and also have reduced water absorbing property, high coating flatness, and high-adhesion. Further, since the compound is capable of reducing an amount of polymerization initiator due to its high reactivity, the composition has high transparency and is usable as a material for forming a coating composition, a coating material, an adhesive, an optical lens, an optical waveguide, and the like.

By reacting the specific oxetane ester sulfonate with the specific phenol with the use of the cesium salt as a base, it is possible to synthesize the trisoxetane compound at high yield without complicated operation.

Furthermore, when at least one of the cladding layer and the core in the optical waveguide is constituted of the resin composition containing the trisoxetane compound represented by the formula (1), it is possible to stably cure the optical waveguide into an identical shape and to achieve stable waveguide characteristic and the like.

Hereinafter, embodiments of the invention will be described.

The trisoxetane compound of the invention is a compound represented by the following formula (1):

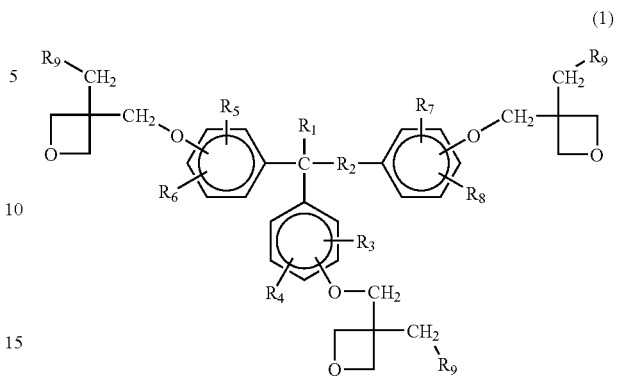

wherein $R_1$ and $R_3$ to $R_8$ are the same or different and each represents a hydrogen atom or an alkyl group having 1 to 6 carbon atom(s) with the proviso that at least one of $R_3$ to $R_8$ is an alkyl group having 1 to 6 carbon atom(s);

$R_2$ represents a divalent aliphatic chained organic group having 0 to 16 carbon atom(s); and $R_9$'s each represents a hydrogen atom or an alkyl group having 1 to 6 carbon atom(s).

The trisoxetane compound of the invention has a structure having three oxetane rings in one molecule thereof. In the formula (1), $R_1$ and $R_3$ to $R_8$ are the same or different and each represents a hydrogen atom or an alkyl group having 1 to 6 carbon atom(s), and at least one of $R_3$ to $R_8$ is an alkyl group having 1 to 6 carbon atom(s). $R_1$ may preferably be a methyl group, and at least one of $R_3$ to $R_8$ may preferably be a methyl group. $R_9$'s each represents a hydrogen atom or an alkyl group having 1 to 6 carbon atom(s), and examples of $R_9$ include a methyl group, an ethyl group, a propyl group, and a butyl group, in which a methyl group or a ethyl group is preferred. $R_2$ is a divalent aliphatic-chained organic group having 0 to 16 carbon atom(s), and particularly, the number of carbon atom(s) may preferably be 1 to 4. In $R_2$, the divalent aliphatic chained organic group having no carbon atom (the number of carbon atom is 0) means a single bond.

It is possible to produce the trisoxetane compound represented by the formula (1) by using as synthesis materials a phenolic compound represented by the formula (2):

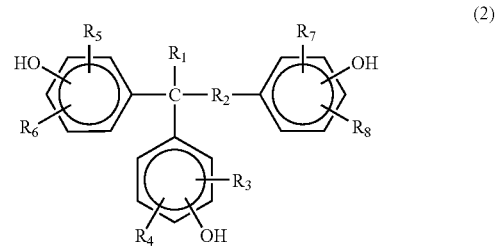

wherein $R_1$ and $R_3$ to $R_8$ are the same or different and each represents a hydrogen atom or an alkyl group having 1 to 6 carbon atom(s) with the proviso that at least one of $R_3$ to $R_8$ is an alkyl group having 1 to 6 carbon atom(s), and $R_2$ represents a divalent aliphatic chained organic group having 0 to 16 carbon atom(s); ether sulfonate of 3-alkyl-3-hydroxymethyloxetane represented by the following formula (3):

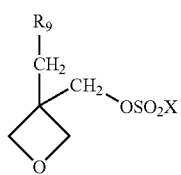

(3)

wherein $R_9$ represents a hydrogen atom or an alkyl group having 1 to 6 carbon atom(s), and X represents a methyl group, an ethyl group, a phenyl group, or a tolyl group; and a cesium salt as a base and reacting them.

Although an alkali metal such as sodium hydroxide and potassium hydroxide, which has been conventionally used, may be used as the base, a cesium salt is preferably used as the base in the invention. By using the cesium salt, it is possible to synthesize the trisoxetane compound at high yield without performing complicated operation. In this case, the synthesis of the materials is performed by, for example, (i) reacting the phenolic compound with the cesium salt to thereby obtain a cesium phenolate and then reacting the cesium phenolate with oxetane ester sulfonate, or (ii) reacting oxetane ester sulfonate with the phenolic compound under the presence of the cesium salt. Preferably, the synthesis is performed in accordance with the process (i). The synthesis is ordinarily performed in an organic solvent (reaction solvent), and water and the like are added to the reaction liquid after the reaction to separate the reaction liquid into a water phase and an organic phase, followed by extraction of a desired trisoxetane compound from the organic phase.

Examples of the cesium salt include cesium carbonate, cesium hydroxide, cesium fluoride, and cesium formate. Among them, cesium carbonate may preferably be used since it enables to obtain the desired trisoxetane compound at high yield.

An amount of the cesium salt to be used may preferably be in the range of 0.8 to 2.0 mol, more preferably be in the range of 1.0 to 1.5 mol, with respect to 1 mol of the phenolic hydroxyl group of the phenolic compound represented by the formula (2).

The phenolic compound represented by the formula (2) is not particularly limited, and examples thereof include tris(3-methyl-4-hydroxyphenyl)methane, tris(2-methyl-4-hydroxyphenyl)methane, 1,1-bis(3-methyl-4-hydroxyphenyl)-2-(hydroxyphenyl)ethane, 1,1,1-tris(3-methyl-4-hydroxyphenyl)ethane, 1-(4-hydroxyphenyl)-3,3-bis(3-methyl-4-hydroxyphenyl)butane, 1,3,3-tris(3-methyl-4-hydroxyphenyl)butane, 1-(4-hydroxyphenyl)-3,3-bis(3,5-dimethyl-4-hydroxyphenyl)butane, 1,3,3-tris(3,5-dimethyl-4-hydroxyphenyl)butane, 1,4,4-tris(3-methyl-4-hydroxyphenyl)pentane, and 1-(4-hydroxyphenyl)-4,4-bis(3-methyl-4-hydroxyphenyl)pentane. These may be used alone or in combination of two or more thereof.

Specific examples of the ester sulfonate of 3-alkyl-3-hydroxymethyloxetane represented by the formula (3) include 2-(3-oxetanyl)propylmesylate, 2-(3-oxetanyl)propylphenyl sulfonylate, 2-(3-oxetanyl)propyltosylate, 2-(3-oxetanyl)butylmesylate, and 2-(3-oxetanyl)butyltosylate. These may be used alone or in combination of two or more thereof.

In this regard, it is possible to synthesize the ester sulfonate of 3-alkyl-3-hydroxymethyloxetane represented by the formula (3), for example, in accordance with the method described in Organic Synthesis, Collective vol. 1, pp. 145 (1941), herein incorporated by reference.

An amount of the ester sulfonate of 3-alkyl-3-hydroxymethyloxetane represented by the formula (3) to be used may preferably be in the range of 1.5 to 2.0 mol, more preferably be in the range of 1.0 to 1.5 mol, with respect to 1 mol of the phenolic hydroxyl group of the phenolic compound represented by the formula (2).

A reaction temperature in the production of the trisoxetane compound of the invention may preferably be in the range of 0° C. to 120° C., more preferably be in the range of 60° C. to 100° C. In the case of reacting the phenolic compound with the cesium salt to thereby obtain the cesium phenolate, a reaction temperature may preferably be set in the range of 0° C. to 120° C., more preferably be in the range of 40° C. to 100° C. A pressure during the reactions is not particularly limited and may be any one of an ordinary pressure, an increased pressure, and a reduced pressure. A reaction atmosphere is not particularly limited and may be a nitrogen atmosphere or an air atmosphere.

In the synthesis of the trisoxetane compound of the invention, an alkali metal such as sodium and potassium; an alkali metal hydride such as lithium hydride and sodium hydride; an alkali metal hydroxide such as sodium hydroxide and potassium hydroxide; an alkali metal carbonate such as sodium carbonate; or the like may be added as a synthesis material according to the necessity.

Further, as a water-organic phase transfer catalyst, a quaternary ammonium salt, a quaternary phosphonium salt, or the like may be added according to the necessity. Examples of the quaternary ammonium salt include, but not particularly limited to, tetraalkylammonium halide such as tetrabutylammonium bromide (TBAB) and tetraethylammonium bromide; and aralkyltrialkylammonium halide such as benzyltrimethylammonium chloride. The quaternary phosphonium salt is not also particularly limited, and examples thereof include tetraarylphosphonium halide such as tetraphenylphosphonium bromide.

Further, in the production of the trisoxetane compound of the invention, the reaction solvent is ordinarily used as described above. The reaction solvent is not particularly limited, and preferred examples thereof include aromatic hydrocarbon such as toluene and xylene; ether such as tetrahydrofuran and dibutylether; and an aprotic polar solvent such as N-methylpyrrolidone, N-methyl-2-pyrrolidone, N,N-dimethylformamide and N,N-dimethylacetoamide. These may be used alone or in combination of two or more thereof.

As mentioned above, it is possible to collect the trisoxetane compound synthesized from the above-described materials by adding water or ethyl acetate to the reaction liquid; separating the liquid into a water phase and an organic phase; extracting the organic phase; and drying the extracted organic phase with anhydrous magnesium sulfate.

It is possible to effectively use the thus-obtained trisoxetane compound as a material for a photocurable resin and a heat curable resin each constituting a coating composition, a coating material, an adhesive, a lens, an optical waveguide, and the like.

Among all, with regard to an optical waveguide including, as shown in FIG. 1, a substrate 1, a cladding layer 2 disposed on the substrate 1, and a core 3 having a predetermined patterning and disposed on the cladding layer 2 for transmitting an optical signal, when the resin composition containing the trisoxetane compound is used for forming at least one of the cladding layer 2 and the core 3, the compound is particularly advantageous for forming a thick film since the compound has a high molecular weight to achieve a high viscosity. Further, advantageous effects such as easy curing into an identical shape and stable waveguide characteristics are achieved. In this regard, it is necessary to regulate a refractive index of the cladding layer 2 to be smaller than that of the core 3.

It is preferable that at least one of the cladding layer 2 and the core 3 is constituted of a resin composition containing the trisoxetane compound and a compound having an epoxy group or a vinylether group, since it is possible to obtain a cured material excellent in heat resistance and moisture resistance as well as to improve exposure sensitivity. As the compound having an epoxy group, it is possible to use any of those exhibiting compatibility with the compound of the invention which is represented by the formula (1). More specifically, examples of the epoxy compound having one epoxy group include phenylglycidylether and butylglycidylether; examples of the epoxy compound having two or more epoxy groups include bisphenol A diglycidylether, bisphenoxyethanolfluorene diglycidylether, trimethylolpropane triglycidylether, and bisphenolfluorene tetraglycidylether; and 3,4-epoxycyclohexenylmethyl-3',4'-epoxycyclohexenecarboxylate, an adduct of 1,2-epoxy-4-(2-oxylanyl)cyclohexane of 2,2-bis(hydroxymethyl-1-butanol, and the like are preferably used as the compound having an alicyclic epoxy group. As the compound having the vinylether group, it is possible to use any of those exhibiting compatibility with the compound of the invention which is represented by the formula (1). More specifically, examples of the compound having one vinylether group include hydroxyethylvinylether, hydroxybutylvinylether and dodecylvinylether. As the compound having two or more vinylether groups, cyclohexanedimethanol divinylether, triethyleneglycol divinylether, novolac type divinylether, and the like are preferably used. These compounds may be used alone or in combination of two or more thereof.

Figure 2A:
FIGS. 2A through 2F are diagrams for illustrating production steps of the optical waveguide of the invention.
Figure 2B:
Figure 2C:
Figure 2D:
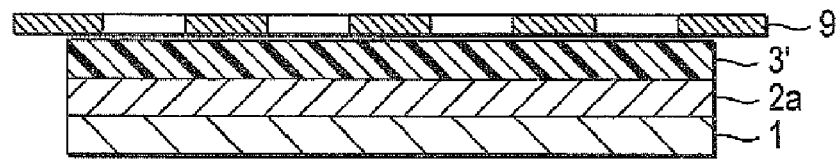
Figure 2E:
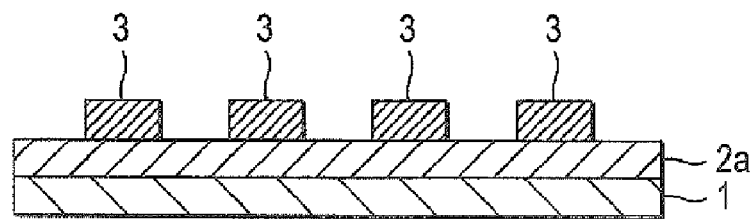
Figure 2F:
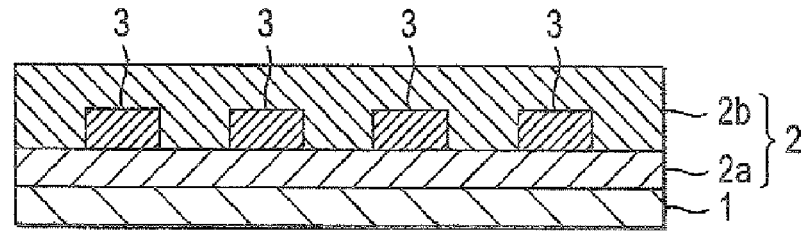

It is possible to produce the optical waveguide by the steps shown in FIGS. 2A through 2F, for example. That is, a substrate 1 is prepared as shown in FIG. 2A, and an undercladding layer 2a (lower portion of a cladding layer 2) is then disposed on the substrate 1 as shown in FIG. 2B. A layer 3' constituted of a resin composition for forming a core 3 is disposed on the undercladding layer 2a as shown in FIG. 2C. A photo mask 9 is disposed on the resin composition layer 3' for exposing a predetermined pattern (optical waveguide pattern) as shown in FIG. 2D, followed by irradiating the resin composition layer 3' with ultraviolet ray via the photomask 9 and heating. After that, an unexposed part of the resin composition layer 3' is dissolved and removed with the use of a development liquid to form the core 3 as shown in FIG. 2E. An overcladding layer 2b (upper portion of the cladding layer 2) is then disposed on the core 3 as shown in FIG. 2F. Thus, it is possible to obtain a desired optical waveguide.

It is possible to form each of the layers on the substrate 1 by a conventional method such as spin coating and coater. The optical waveguide may be formed into a film-like optical waveguide by peeling off the substrate 1. The film-like optical waveguide is excellent in flexibility.

The thus-obtained optical waveguide may be used as a linear optical waveguide, a curved optical waveguide, a crossing optical waveguide, a Y branch optical waveguide, a slab optical waveguide, a mach zender type optical waveguide, an AWG type optical waveguide, a grating, an optical waveguide lens, and the like. Examples of optical elements using the optical waveguides include a wavelength filter, an optical switch, an optical brancher, an optical multiplexer, an optical multiplexer/brancher, an optical amplifier, an waveguide converter, a waveguide divider, an optical splitter, a directional coupler, an optical transmission module having a laser diode and a photo diode that are hybrid-integrated, and the like.

EXAMPLES

The invention will be explained below in more detail by reference to Examples, but the invention should not be construed as being limited by the following Examples.

In advance of the examples, 2-(3-oxetanyl)butyltosylate which is ester sulfonate of 3-alkyl-3-hydroxymethyloxetane was synthesized as described below.

Synthesis of 2-(3-oxetanyl)butyltosylate

Into a 2000 ml three-neck flask having a thermometer, a cooler, a stirring device, and a dripping funnel, 190.65 g (1.0 mol) of p-toluene sulfonate chloride, 32.24 g (0.1 mol) of tetramethylammonium bromide, and 400 ml of toluene were poured and cooled to 5° C. with stirring in an ice bath. After pouring 116.16 g (1.0 mmol) of 3-ethyl-hydroxymethyloxetane into the three-neck flask, 130 ml of a 35 wt % sodium hydroxide solution was dripped into the three-neck flask in 30 minutes. After the dripping, stirring was continued for 1 hour at the same temperature and then for 16 hours at a room temperature. After the reaction, 800 ml of water was poured into the flask followed by violent stirring. The mixture was left to stand to separate a water phase from an organic phase. The organic phase was washed with 400 ml of water and then dried with anhydrous magnesium sulfate over night. Then, the magnesium sulfate was removed by filtration, and the filtrate was concentrated. The thus-obtained crude product was separated and purified by silica gel column chromatography (eluting solution: hexane/ethyl acetate) to obtain a desired substance, i.e. 243.3 g (yield: 90%) of 2-(3-oxetanyl) butyltosylate as a colorless liquid.

Example 1

Into a 200 ml three-neck flask having a thermometer, a cooling tube, and a stirring device, 3.62 g (10 mmol) of 1-(4-hydroxyphenyl)-3,3-bis(3-methyl-4-hydroxyphenyl) butane and 15 ml of N-methyl-2-pyrrolidone were poured and heated to 80° C. with stirring under a nitrogen atmosphere until the substances were perfectly dissolved. After the dissolution, 11.73 g (36 mmol) of cesium carbonate was added, followed by stirring under a nitrogen atmosphere at 80° C. for 30 minutes. To the mixture, 8.92 g (33 mmol) of 2-(3-oxetanyl)butyltosylate synthesized in advance was added, followed by stirring under the nitrogen atmosphere at 80° C. for 20 hours. After the reaction, the mixture was cooled to a room temperature (25° C.), and then 100 ml of ethyl acetate and 50 ml of distilled water were added to the mixture. The mixture was left to stand to be separated into a water phase and an organic phase. The separated organic phase was extracted and then washed with water and a saturated saline, followed by drying with anhydrous magnesium sulfate over night. Then, the magnesium sulfate was removed by filtration, and the solvent was distilled off to obtain a reaction crude product.

As a result of an analysis of the thus-obtained crude product by thin layer chromatography, one spot was confirmed. Also, 5.92 g (yield: 90%) of a white solid matter was obtained by recrystallizing the crude product after purification by silica gel chromatography (eluting solution: n-hexane/ethyl acetate). A purity of the compound detected by liquid chromatography was 99% or more.

It was confirmed from the following results of an analysis using $^1$H-NMR and $^{13}$C-NMR (products of JEOL Ltd.) that the obtained compound was 1-{4-[2-(3-oxetanyl)butoxyphenyl]}-3,3-bis{3-methyl-4-[2-(3-oxetanyl)butoxyphenyl]}butane represented by the following structural formula (7).

$^1$H-NMR (DMSO-d$_6$, 400 MHz): δ(ppm); 0.87 (t, J=7.6 Hz, 3H, CH$_3$), 0.89 (t, J=7.6 Hz, 6H, CH$_3$), 1.60 (s, 3H, CH$_3$), 1.77 (q, J=7.6 Hz, 2H, CH$_2$), 1.80 (q, J=7.6 Hz, 4H, CH$_2$), 2.10 (s, 6H, CH$_3$), 2.25 (s, 4H, CH$_2$), 4.03 (s, 6H, CH$_2$), 4.32 (d, J=6.4 Hz, 2H, CH$_2$), 4.37 (d, J=5.6 Hz, 4H, CH$_2$), 4.41 (d, J=5.6 Hz, 2H, CH$_2$), 4.46 (d, J=6.0 Hz, 4H, CH$_2$), 6.86-6.90 (m, 4H, Ar), 6.98 (m, 4H, Ar), 7.04 (d, J=8.8 Hz, 2H, Ar)

$^{13}$C-NMR (DMSO-d$_6$, 100 MHz): δ(ppm); 7.98, 8.04, 16.00, 26.17, 26.37, 27.34, 29.94, 42.46, 42.62, 43.84, 44.33, 70.02, 70.15, 76.77, 76.80, 110.70, 114.43, 125.02, 125.17, 128.99, 134.74, 141.28, 154.40, 156.85

Structural formula (7)

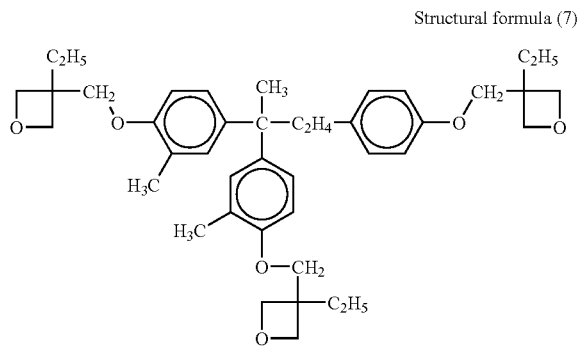

Example 2

An optical waveguide (see FIG. 1) was produced by forming an undercladding layer, a core, and an overcladding layer as described below. Then, evaluation of the optical waveguide was conducted as described below.

Formation of Undercladding Layer

Into cyclohexanone, 70 parts by weight (hereinafter abbreviated to parts) of 1-{4-[2-(3-oxetanyl)butoxyphenyl]}-3,3-bis{3-methyl-4-[2-(3-oxetanyl)butoxyphenyl]}butane obtained in Example 1, 30 parts of 3,4-epoxycyclohexenyl-methyl-3',4'-epoxycyclohexenecarboxylate (product of Daicel Chemical Industries, Ltd.; celoxide 2021P) which is alicyclic epoxy compound, and 1 part of a 50% propion carbide solution of 4,4-bis(di(β-hydroxyethoxy)phenylsulfinio)phenylsulfide-bis-hexafluoroantimonate were dissolved to prepare a polymerizable composition A for cladding layer formation. Then, on a surface of a glass substrate (5 cm×5 cm×thickness of 2 mm), the polymerizable composition A was coated by spin coating, followed by drying at 100° C. for 5 minutes. A whole surface was irradiated with ultraviolet ray at an irradiation amount of 2,000 mJ/cm$^2$, followed by a heat treatment at 100° C. for 30 minutes to form the undercladding layer (see FIG. 2B). A thickness of the undercladding layer measured by using a contact type film thickness meter was 30 μm. A refractive index of the underclad was 1.545 at a wavelength of 633 nm.

Formation of Core

Then, into cyclohexanone, 90 parts of 1-{4-[2-(3-oxetanyl)butoxyphenyl]}-3,3-bis{3-methyl-4-[2-(3-oxetanyl)butoxyphenyl]}butane obtained in Example 1, 10 parts of bisphenoxyethanol fluorene diglycidylether (epoxy equivalent: 320), and 1 part of a 50% propion carbide solution of 4,4-bis[di(β-hydroxyethoxy)phenylsulfinio]phenylsulfide-bis-hexafluoroantimonate were dissolved to prepare a polymerizable composition B for core formation. Then, the polymerizable composition B was coated on the undercladding layer by spin coating (see FIG. 2C). The coating layer was dried at 150° C. for 20 minutes, and then a synthetic quartz-based chrome mask (photomask) on which a linear optical waveguide pattern of 50 μm pitch was printed was disposed on the coating layer (see FIG. 2D), followed by irradiation with ultraviolet ray at an irradiation amount of 2,000 mJ/cm$^2$ by a contact exposure method via the chrome mask and a heat treatment at 150° C. for 30 minutes. After that, in order to eliminate a non-irradiated part, development was performed by using a γ-butylolactone solution, followed by heating at 150° C. for 30 minutes to form a core pattern (see FIG. 2E). A sectional shape of the core pattern was a square having a width of 50 μm and a height of 50 μm, which was measured by using a length measurement microscope. A refractive index of the core was 1.570 at a wavelength of 633 nm.

Formation of Overcladding layer

The polymerizable composition A prepared for the undercladding layer formation was coated on the core and the undercladding layer by spin coating. After drying at 100° C. for 5 minutes, a whole surface was irradiated with ultraviolet ray at an irradiation amount of 2,000 mJ/cm$^2$, followed by a heat treatment at 150° C. for 60 minutes to form an overcladding layer (see FIG. 2F). Thus, the optical waveguide having a relative refractive index Δ of 1.6% was produced.

Evaluation

The optical waveguide was cut by a length of 10 cm using a dicing device (Disco Corporation; model 522), followed by end face processing. Then, a sectional shape of the optical waveguide was observed by using a length measurement microscope to confirm that the optical waveguide was of an embedded multimode optical waveguide with a thickness of the undercladding layer being 30 μm, the size of the core being 50 μm×50 μm; and a thickness of the overcladding layer being 70 μm. An optical propagation loss of the optical waveguide that was measured by an ordinary cut-back method using a laser beam of a wavelength of 850 nm was 0.07 dB/cm. Also, it was possible to use the optical waveguide that was peeled off from the substrate as a film-like waveguide. The film-like waveguide was free from a loss reduction with respect to a bending with R of 20 mm and capable of bending with R of 5 mm, thereby proving its good flexibility.

The trisoxetane compound of the invention is used as a component of a photocurable resin composition or a heat curable resin composition, and each of the resin compositions is usable as a material for forming coating compositions, coating materials, adhesives, optical lenses, optical waveguides, and the like. Examples of the optical waveguides include a linear optical waveguide, a curved optical waveguide, a crossing optical waveguide, a Y branch optical waveguide, a slab optical waveguide, a mach zender type optical waveguide, an AWG type optical waveguide, a grating, and an optical waveguide lens. Examples of optical elements using the optical waveguides include a wavelength filter, an optical switch, an optical brancher, an optical multiplexer, an optical multiplexer/brancher, an optical amplifier, an waveguide converter, a waveguide divider, an optical splitter, a directional coupler, and an optical transmission module having a laser diode and a photo diode that are hybrid-integrated.

While the present invention has been described in detail and with reference to specific embodiments thereof, it will be apparent to one skilled in the art that various changes and modifications can be made therein without departing from the scope thereof.

This application is based on Japanese patent application No. 2006-105203 filed Apr. 6, 2006, the entire contents thereof being hereby incorporated by reference.

What is claimed is:

1. A trisoxetane compound represented by the following formula (1):

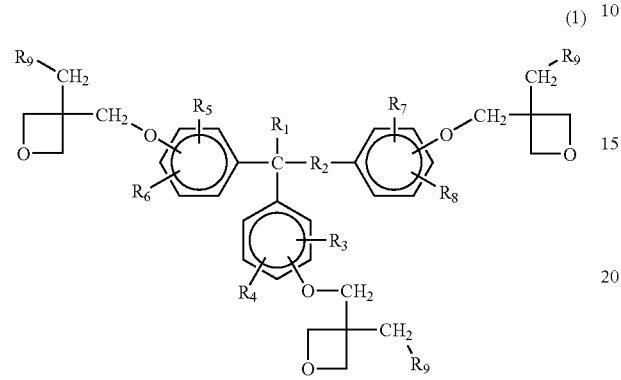

(1)

wherein $R_1$ and $R_3$ to $R_8$ are the same or different and each represents a hydrogen atom or an alkyl group having 1 to 6 carbon atom(s) with the proviso that at least one of $R_3$ to $R_8$ is an alkyl group having 1 to 6 carbon atom(s);

$R_2$ represents a divalent aliphatic chained organic group having 0 to 16 carbon atom(s); and $R_9$'s each represents a hydrogen atom or an alkyl group having 1 to 6 carbon atom(s).

2. A process for producing the trisoxetane compound according to claim 1, which comprises:

reacting a phenolic compound represented by the following formula (2):

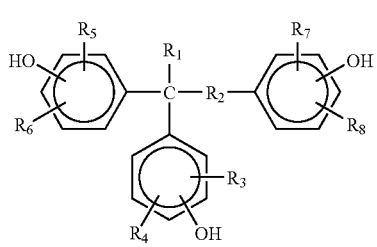

(2)

wherein $R_1$ and $R_3$ to $R_8$ are the same or different and each represents a hydrogen atom or an alkyl group having 1 to 6 carbon atom(s) with the proviso that at least one of $R_3$ to $R_8$ is an alkyl group having 1 to 6 carbon atom(s), and $R_2$ represents a divalent aliphatic chained organic group having 0 to 16 carbon atom(s), with a cesium salt to thereby obtain a cesium phenolate; and reacting the cesium phenolate with an ester sulfonate of 3-alkyl-3-hydroxymethyloxetane represented by the following formula (3):

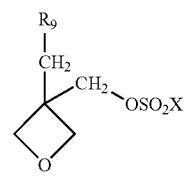

(3)

wherein $R_9$ represents a hydrogen atom or an alkyl group having 1 to 6 carbon atom(s), and X represents a methyl group, an ethyl group, a phenyl group, or a tolyl group.

3. The process according to claim 2, wherein the cesium salt is cesium carbonate.

4. An optical waveguide comprising:
a substrate;
a cladding layer disposed on the substrate; and
a core having a predetermined pattern and disposed on the cladding layer, which transmits an optical signal,
wherein at least one of the cladding layer and the core is constituted of a resin composition containing a trisoxetane compound represented by the following formula (1):

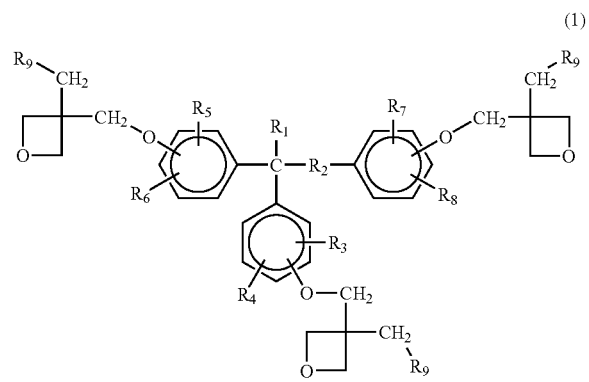

(1)

wherein $R_1$ and $R_3$ to $R_3$ are the same or different and each represents a hydrogen atom or an alkyl group having 1 to 6 carbon atom(s) with the proviso that at least one of $R_3$ to $R_8$ is an alkyl group having 1 to 6 carbon atom(s);

$R_2$ represents a divalent aliphatic chained organic group having 0 to 16 carbon atom(s);

and $R_9$'s each represents a hydrogen atom or an alkyl group having 1 to 6 carbon atom(s).

5. The optical waveguide according to claim 4, wherein at least one of the cladding layer and the core is constituted of a resin composition containing the trisoxetane compound and a compound having an epoxy group or a vinylether group.

* * * * *